(12) United States Patent
Rosenberg et al.

(10) Patent No.: US 7,297,155 B2
(45) Date of Patent: Nov. 20, 2007

(54) MEDICAL USES OF ULTRAVIOLET LIGHT

(76) Inventors: E. William Rosenberg, 6055 Sweetbriar Cove, Memphis, TN (US) 38120; Karl T. Weber, 193 S. Mendenhall, Memphis, TN (US) 38117; Robert M. Sayre, 8621 Loxley Fairway, Cordova, TN (US) 38016; John C. Dowdy, 11212 Ram Hill Cove, Arlington, TN (US) 38002; James G. Shepherd, 3078 Ashley Dr., Edgewood, KY (US) 41017

( * ) Notice: Subject to any disclaimer, the term of this patent is extended or adjusted under 35 U.S.C. 154(b) by 87 days.

(21) Appl. No.: 11/176,434

(22) Filed: Jul. 7, 2005

(65) Prior Publication Data

US 2006/0015156 A1   Jan. 19, 2006

Related U.S. Application Data

(60) Provisional application No. 60/586,384, filed on Jul. 8, 2004.

(51) Int. Cl.
  *A61N 5/061* (2006.01)
(52) U.S. Cl. .......................................... 607/94; 128/898
(58) Field of Classification Search ............ 607/88–94; 128/898
  See application file for complete search history.

(56) References Cited

U.S. PATENT DOCUMENTS

| | | | |
|---|---|---|---|
| 6,402,774 B1 * | 6/2002 | Caldironi | 607/91 |
| 6,436,127 B1 * | 8/2002 | Anderson et al. | 607/89 |
| 6,447,537 B1 * | 9/2002 | Hartman | 607/94 |
| 6,468,508 B1 * | 10/2002 | Laughlin | 424/59 |
| 6,835,202 B2 * | 12/2004 | Harth et al. | 607/91 |
| 2003/0004501 A1 * | 1/2003 | Wilkens et al. | 606/9 |
| 2003/0060853 A1 * | 3/2003 | Unvert et al. | 607/20 |
| 2003/0155536 A1 * | 8/2003 | Laudano et al. | 250/504 R |
| 2004/0256582 A1 * | 12/2004 | Laudano et al. | 250/504 R |

OTHER PUBLICATIONS

Rostand, Stephen G., "Ultraviolet Light May Contribute to Geographic and Racial Blood Pressure Differences", *Hypertension*, 1997, vol. 30, pp. 150-156.
Krause, Rolfdieter, et al.,"Ultraviolet B and blood pressure", *Lancet*, 0099-5355, Aug. 29, 1998, vol. 352, Issue 9129, pp. 709-710.
Flitney, Frederick W., et al., "Nitric oxide and the mechanism of rat vascular smooth muscle photorelaxation", *J. Physiol.*, 2003, vol. 550, published online Jun. 24, 2003, pp. 819-828.
Buyukafsar, Kansu, et al., "Mediation of nitric oxide from photosensitive stores in the photorelaxation of the rabbit corpus cavernosum", *European Journal of Pharmacology*, 2003, vol. 459, pp. 263-267.
Ergenekon, Ebru, et al., "Nitric Oxide Production in Newborns under Phototherapy", *Nitric Oxide: Biology and Chemistry*, vol. 6, No. 1, (2002), published online Aug. 30, 2001, pp. 69-72.

* cited by examiner

*Primary Examiner*—Henry M Johnson, III
(74) *Attorney, Agent, or Firm*—Pearne & Gordon LLP

(57) ABSTRACT

A method of treating a patient having a condition selected from the group including hypertension, hypertensive crises, angina pectoris, chronic arthritis, erectile dysfunction, cerebral ischemia and chronic skin ulcers comprising the step of administering to the patient a therapeutically effective amount or dose, or series of amounts or doses, of ultraviolet light.

8 Claims, 1 Drawing Sheet

MEDICAL USES OF ULTRAVIOLET LIGHT

This application claims the benefit of U.S. Provisional Patent Application Ser. No. 60/586,384 filed Jul. 8, 2004, the contents of which are incorporated herein by reference in their entirety.

BACKGROUND OF THE INVENTION

1. Field of Invention

The present invention relates to the medical uses of ultraviolet light.

2. Description of Related Art

There is well-documented evidence that blood pressure tends to be lower in the summer than winter and higher as one moves farther from the equator. Previous published studies have attributed these findings to the increased vitamin D levels associated with sun exposure.

Based on our experiments we have found that there is an immediate (within minutes) fall in systolic blood pressure in both black- and white-skinned individuals and in both normotensive and hypertensive subjects who were exposed to measured, modest doses of artificially produced sunlight wavelengths. The ultraviolet light to be used in this invention is preferably UV-A light having wavelengths of 315-400 nm, more preferably 320-400 nm.

Such an effect could not be attributed to the production of vitamin D, which must go through several metabolic steps in the skin, liver and kidney to become active.

A more likely explanation of what we observed is a result of the almost immediate effect of nitric oxide (NO) in dilating blood vessels. There are two mechanisms described by which NO is released in blood vessels. One is the induction of NO formation by the enzyme called iNOS. The other is the release of preformed NO precursors when stimulated by near-visible ultraviolet light in a process called "photorelaxation". The familiar sunburn reaction has been shown to be mediated by an iNOS effect. Thus there are adequate explanations for the immediate blood pressure lowering effect we saw when our subjects were exposed to physiologic amounts of artificial sunlight.

We also believe there to be a systemic effect from NO released in the skin. One treatment for coronary artery disease-caused chest pain (angina pectoris) is to apply nitroglycerin ointment to the chest wall over the heart. The nitroglycerin ointment releases NO through the skin and it has an effect on the heart.

NO is a profound promoter of increased blood flow. It also has been described as having anti-carcinogenic, anti-inflammatory and anti-arteriosclerotic effects by way of its chemical action of neutralizing oxygen-free radicals.

SUMMARY OF THE INVENTION

A method of treating a patient having a condition selected from the group including hypertension, hypertensive crises, angina pectoris, chronic arthritis, erectile dysfunction, cerebral ischemia and chronic skin ulcers. The method comprises the step of administering to the patient a therapeutically effective amount or dose, or series of amounts or doses, of ultraviolet light.

DETAILED DESCRIPTION OF THE PREFERRED EMBODIMENTS OF THE INVENTION

Figure 1:
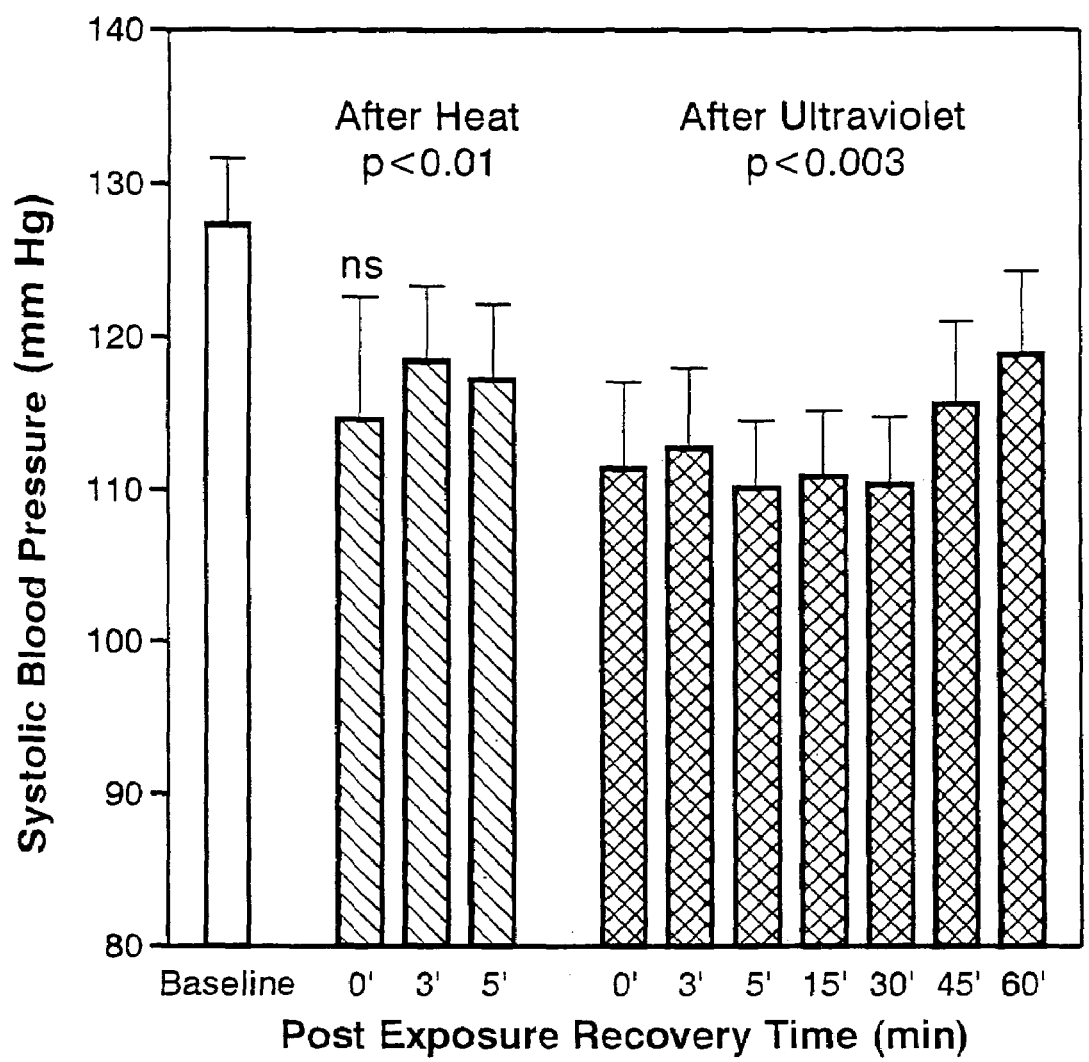
FIG. 1 is a chart summarizing systolic blood pressure readings post exposure.

The present invention comprises a novel treatment method for a variety of medical conditions, all of which are expected to be improved by the nearby increase of NO levels resulting from or via exposure of ultraviolet light to the skin. These conditions include hypertension, hypertensive crises, angina pectoris, chronic arthritis, erectile dysfunction, cerebral ischemia and chronic skin ulcers as well as other similar or related conditions. The present invention includes a method of treating these conditions by applying or providing to the patient via or on their skin a medically effective amount of ultraviolet radiation, preferably UV-A ultraviolet radiation, such as the amounts described in the attachment hereto. Preferably the technology to be employed is an improvement over the ultraviolet tanning booth used in our blood pressure study, which is a less preferred source. In accordance with the present invention, the mostly UV-A light will preferably be generated through presently available small, high output sources such as fluorescent-FS bulbs and high and medium pressure mercury arc lamps. Other UV light sources known in the art may be used. In appropriate situations the light will be carried in or through woven fiber active pads or soft, pliable light-transmitting sponges that can be placed in direct apposition to relevant body parts such as the chest wall, forehead, male genitalia, painful joint, ulcer site etc. An appropriate flux of less-than-erythrogenic UV light would thus be made available to increase the NO levels in that vicinity. Alternatively, a true "sunbath" can be achieved by the use of a clear plastic bathtub liner that would diffuse the UV light to every area of the submerged torso through the clear bath water.

Increased levels of blood pressure vary with latitude; toward the equator there is less hypertension. Krause et al. attributed this effect to higher vitamin D levels found in sunnier climates.

This report examines potential alternative roles of ultraviolet (UV) exposure and whether a single exposure can achieve a reduction in blood pressure. Nineteen white and black normotensive and hypertensive (treated and untreated) volunteers were selected. The U.S. Food and Drug Administration has adopted categorizing different races and complexions into six skin types based upon ease of sunburn and propensity to develop pigmentation. Skin types I and II are the fairest and are at the greatest risk for sunlight-induced injury, whereas skin types V and VI are the darkest and have little risk for sunlight-induced injury. Selected volunteers ranged over the entire set of skin types based upon their inherent propensity to sunburn and tan. Two sources of exposure were used: two 250-watt infrared, reflectorized incandescent-type lamps; and a UV-A/UV-B phototherapy cabinet.

The protocol required a baseline blood pressure measurement followed by an infrared exposure of 8 minutes and 20 seconds that was immediately followed by blood pressure measurements at 0, 3, and 5 minutes. Following this, volunteers re-entered the UV-A/UV-B cabinet to receive an exposure of a mixture of UV-B and UV-A radiation. Fair-skinned, white volunteers of skin types I and II received a 7.8 J/cm$^2$ exposure involving only the UV-A lamps, or 1.5 standard erythema doses, an erythemic effective exposure of 10 mJ/cm$^2$. It is approximately ½ of a minimal erythemal dose of a fair-skinned person. Skin types III and IV received the same 7.8 J/cm$^2$ dose from the UV-A lamps plus an additional 0.02 J/cm$^2$ dose from the UV-B lamps, or 2.25 standard erythema doses. For volunteers with skin types V and VI, the same 7.8 J/cm$^2$ dose was administered from the UV-A lamps, and a 0.04 J/cm$^2$ dose of UV-B radiation was administered, for a total of 3 standard erythema doses. Thus, the UV dose maintained constant UV-A dosage and varied the amount of erythemic UV-B dosage with the UV-B lamps. The UV doses administered were approximately equivalent to a 12- to 24-minute exposure of sunlight.

FIG. 1 summarizes the study results. We did not observe any differences based on the sex, race, or blood pressure status of individual volunteers. We did observe a moderate drop in blood pressure following exposure to the infrared lamps at 3 and 5 minutes. Because blood pressure measurements were made only for a 5-minute period following infrared exposure, we cannot state how long that reduction would have lasted. The reduction following UV exposure was significantly greater (p<0.003) and appeared to last considerably longer. One hour after exposure, systolic blood pressure was increasing, but it was still lower than the initial recording. At this time, we cannot state how long this reduction in systolic blood pressure would last. A statistically significant reduction (p<0.05) in diastolic blood pressure was seen only at 15 and 30 minutes following UV exposure. Krause et al. reported substantial reductions in both systolic and diastolic blood pressures following a series of UV-B exposures using a lamp that may have been spectrally similar to our UV-A source.

A light-induced nitric oxide-mediated phenomenon termed photorelaxation occurs in vascular and other smooth muscle. A comparable mechanism seems likely to account for the reduction in blood pressure in newborns under phototherapy and in this study. Photorelaxation is a response primarily to UV-A radiation and raises the possibility of achieving therapeutic effects from currently available phototherapy devices and even from indoor tanning units.

With reference to FIG. 1, statistically significant but modest decreases in systolic blood pressure were observed following exposure to infrared lamps at 3 and 5 minutes after exposure (p<0.01). Following ultraviolet exposure, all volunteers showed a highly significant decrease in systolic blood pressure (p<0.003). Bars indicate mean, error bars indicate SEM.

The present invention includes the medical use of UV light as described herein to treat the conditions described herein. The UV light, preferably UV-A light, can be provided to the skin by directly shining on the skin or being transmitted through carriers such as fiber optic carriers as known in the art or other carriers or transmitters known in the art to transmit light, such as a light blanket as known in the art.

What is claimed is:

1. A method of treating a patient suffering from hypertension or hypertensive crises, said method comprising the steps of:
    a) determining, based on an evaluation of the patient, that the patient is suffering from hypertension or hypertensive crises;
    b) determining the skin type of the patient;
    c) determining and selecting a therapeutically effective dosage of artificial UV-A ultraviolet light based on the condition of the patient and the skin type of the patient;
    d) administering to said patient said selected dosage of artificial UV-A ultraviolet light; and
    e) measuring the blood pressure of said patient within 30 minutes of the conclusion of said administering step.

2. The method of claim 1, wherein said administering is via exposure of ultraviolet light to the skin.

3. The method of claim 1, further comprising a step of measuring the blood pressure of said patient before administering to said patient said dosage of artificial UV-A ultraviolet light.

4. The method of claim 3, wherein the administered dosage is effective to lower the blood pressure of the patient within 30 minutes of the conclusion of said administering step.

5. The method of claim 1, wherein said selected dosage includes at least about 1.5 standard erythema doses.

6. The method of claim 1, wherein said selected dosage includes at least about 7.8 J/cm$^2$ exposure from a UV-A lamp.

7. The method of claim 1, wherein the administered dosage is effective to lower the blood pressure of the patient within 30 minutes of the conclusion of said administering step.

8. The method of claim 1, wherein the administered dosage is effective to lower the blood pressure of the patient within 15 minutes of the conclusion of said administering step.

* * * * *